(12) United States Patent
Hamilton

(10) Patent No.: US 6,451,854 B1
(45) Date of Patent: Sep. 17, 2002

(54) α-AMINO ACID PHENYL ESTER DERIVATIVES

(75) Inventor: Niall Morton Hamilton, Glasglow (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/744,004

(22) PCT Filed: Jul. 16, 1999

(86) PCT No.: PCT/EP99/05051

§ 371 (c)(1),
(2), (4) Date: Jan. 18, 2001

(87) PCT Pub. No.: WO00/05196

PCT Pub. Date: Feb. 3, 2000

(30) Foreign Application Priority Data

Jul. 22, 1998 (EP) ............................................. 98305837

(51) Int. Cl.$^7$ .................... A61K 31/325; C07C 229/38; A61P 23/00
(52) U.S. Cl. ......................... 514/532; 558/390; 560/38; 560/39; 560/169; 560/172
(58) Field of Search ............................ 558/390; 560/38, 560/39, 169, 172; 514/532

(56) References Cited

FOREIGN PATENT DOCUMENTS

| | | |
|---|---|---|
| BE | 664244 | 9/1965 |
| GB | 1 102 011 | 2/1968 |
| GB | 1160468 | 8/1969 |

OTHER PUBLICATIONS

Loveless et al., "Prevention by sulfhydryl compounds" Chemical Abstracts, vol. 84, No. 76, 1976 (abstract only).
Coscia, L. et al., "Local Anesthetic Activity of Arylic Esters of N,N–disubstituted α–amino acids," *Boll Chim Farm*, 1968, 107:310–319.
Smith, T.C. and Wollman, H., "History and Principles of Anesthesiology," in *Goodman and Gilman's The Pharmacological Basis of Therapeutics*, 1985, pp. 260–275, 7th Ed., Gilman, A.G. et al., eds., Macmillan Publishing Co., New York.
Marshall, B.E. and Wollman, H., "General Anesthetics," in *Goodman and Gilman's The Pharmacological Basis of Therapeutics*, 1985, pp. 276–301, 7th Ed., Gilman, A.G. et al., eds., Macmillan Publishing Co., New York.
Ritchie, J.M. and Greene, N.M., "Local Anesthetics," in *Goodman and Gilman's The Pharmacological Basis of Therapeutics*, 1985, pp. 302–321, 7th Ed., Gilman, A.G. et al., eds., Macmillan Publishing Co., New York.
Rees, D.C. et al. (1996). "Drugs in Anesthetic Practice," *Ann. Reports in Med. Chem.*, vol. 31, Chapter 5 (Academic Press, Inc., publ.), pp. 41–50.
Brancaccio, G. et al. (1964). "Anestetici Locali," *Il Framaco*, Ed. Sc., Vol. XIX, pp. 986–1002.

*Primary Examiner*—Robert W. Ramsuer
*Assistant Examiner*—Andrea D Small
(74) *Attorney, Agent, or Firm*—William M. Blackstone; Jeffrey L. Ihnen

(57) ABSTRACT

The present invention relates to α-amino acid phenyl ester derivatives having general formula (I) wherein $R_1$ is $(C_{1-3})$ alkyloxy; $R_2$ is $(C_{1-3})$alkyl, $(C_{1-3})$alkyloxy or $(C_{2-3})$alkenyl; $R_3$ is hydrogen, $(C_{1-3})$alkyl, $(C_{1-3})$alkyloxy or $(C_{2-3})$alkenyl; $R_4$ is $(C_{1-6})$alkyl; $R_5$ and $R_6$ are independently $(C_{1-6})$alkyl, $(C_{2-6})$alkenyl, $(C_{2-6})$alkynyl or aralkyl, each of which may be optionally substituted with $(C_{1-3})$alkyloxy, $(C_{1-3})$ alkyloxycarbonyl, cyano or $NR_7R_8$; $R_7$ and $R_8$ are independently $(C_{1-6})$alkyl; or a pharmaceutically acceptable salt thereof. The invention also relates to pharmaceutical compositions comprising said derivatives, and to the use of these α-amino acid phenyl ester derivatives as hypnotics for the induction and maintenance of general anaesthesia.

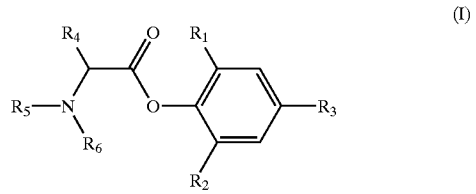

(I)

9 Claims, No Drawings

α-AMINO ACID PHENYL ESTER DERIVATIVES

This application is 371 of PCT/EP99/05051 Jul. 16, 1999.

The invention relates to α-amino acid phenyl ester derivatives, to pharmaceutical compositions containing the same, as well as to the use of these α-amino acid phenyl ester derivatives as hypnotics for the induction and maintenance of general anaesthesia.

It has been reported (G. Brancaccio and A. Larizza, II Farmaco 1964, 19, 986–1002) that α-amino acid phenyl ester derivatives, wherein the amino group is either dialkylated or is part of an heterocyclic system (GB 1,102,011: Richardson-Merrell S.p.A.), possess local anaesthetic activity, with piperazinyl derivatives proving the most active. In GB 1,160,468 (May & Baker Ltd.) an α-amino acid phenyl ester wherein the amino group is part of a morpholinyl ring, i.e. 2,6-dimethoxyphenyl 2-morpholinopropionate, is disclosed as an intravenous general anaesthetic having a short duration of activity with rapid, smooth recovery. The hypnotic properties of this compound are attained at rather high dose levels and consequently there exists a need for new water soluble intravenous general anaesthetics with improved potency.

The present invention provides α-amino acid phenyl ester derivatives having the general formula I

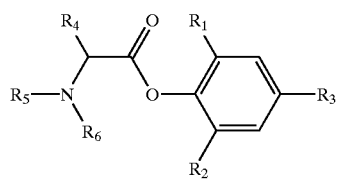

Formula I wherein
$R_1$ is $(C_{1-3})$alkyloxy;
$R_2$ is $(C_{1-3})$alkyl, $(C_{1-3})$alkyloxy or $(C_{2-3})$alkenyl;
$R_3$ is hydrogen, $(C_{1-3})$alkyl, $(C_{1-3})$alkyloxy or $(C_{2-3})$alkenyl;
$R_4$ is $(C_{1-6})$alkyl;
$R_5$ and $R_6$ are independently $(C_{1-6})$alkyl, $(C_{2-6})$alkenyl, $(C_{2-6})$alkynyl or aralkyl, each of which may be optionally substituted with $(C_{1-3})$alkyloxy, $(C_{1-3})$alkyloxycarbonyl, cyano or $NR_7R_8$;
$R_7$ and $R_8$ are independently $(C_{1-6})$alkyl;
or a pharmaceutically acceptable salt thereof, with the exclusion of 2,6-dimethoxyphenyl 2-(diethylamino) propionate and 2,6-dimethoxyphenyl 2-(diethylamino) butyrate.

Since 2,6-dimethoxyphenyl 2-(diethylamino)propionate and 2,6-dimethoxyphenyl 2-(diethylamino)butyrate have been described as local anaesthetics by G. Brancaccio and A Larizza (vide supra), no protection is sought for these compounds per se.

The α-amino acid phenyl ester derivatives of formula I, having a dialkylated amino group, were surprisingly found to be potent intravenous hypnotics with quick onset, and a short duration of action with rapid, smooth recovery.

The term $(C_{1-6})$alkyl, as used in the definition of formula I, means a branched or unbranched alkyl group having 1–6 carbon atoms, like hexyl, pentyl, isobutyl, tertiary butyl, propyl, isopropyl, ethyl and methyl. The term $(C_{1-3})$alkyl means an alkyl group having 1–3 carbon atoms, like n-propyl, isopropyl, ethyl and methyl. In the term $(C_{1-3})$ alkyloxy as used in formula I, $(C_{1-3})$alkyl has the meaning as previously given, preferably methyl. The term $(C_{2-6})$ alkenyl means a branched or unbranched alkenyl group having 2–6 carbon atoms, like for example hexenyl, pentenyl, butenyl, 1,3-butadienyl, 1-methyl-propen-2-yl, propen-2-yl(allyl), propen-1-yl or ethenyl(vinyl). Alkenyl groups having at least 3 carbon atoms may be in the E- or Z-form, or a mixture thereof. The term $(C_{2-3})$alkenyl means an alkenyl group having 2 or 3 carbon atoms, like propen-2-yl, propen-1-yl or ethenyl(vinyl).

The term $(C_{2-6})$alkynyl means a branched or unbranched alkynyl group having 2–6 carbon atoms, like hexynyl, pentynyl, butynyl, propyn-2-yl or ethynyl. The term aralkyl means an aryl$(C_{1-3})$alkyl group, wherein alkyl means a bivalent carbon radical having 1–3 carbon atoms, such as methylene, ethan-1,2diyl, propan-1,3-diyl, ethylidene or propylidene, and wherein aryl means a $C_{6-12}$ aromatic group and includes one or two $C_6$-aromatic rings, like for example phenyl, naphthyl or biphenyl.

Preferred α-amino acid phenyl ester derivatives of the invention correspond to compounds having formula I wherein $R_1$ and $R_2$ are methoxy; and $R_4$ is $(C_{2-3})$alkyl, like ethyl, propyl or isopropyl, and wherein $R_3$, $R_5$ and $R_6$ have the previously given meanings. Further preferred are compounds of formula I wherein $R_1$ and $R_2$ are methoxy, $R_3$ is hydrogen or $(C_{1-3})$alkyl, $R_4$ is $(C_{2-3})$alkyl and wherein $R_5$ and $R_6$ are independently $(C_{1-6})$alkyl or aralkyl, each of which may be optionally substituted with $(C_{1-3})$alkyloxy. More preferred are the compounds wherein $R_1$ and $R_2$ are methoxy, $R_3$ is hydrogen or methyl, $R_4$ is $(C_{2-3})$alkyl, and $R_5$ and $R_6$ are independently methoxyethyl or ethoxyethyl. Especially preferred α-amino acid phenyl ester derivatives of the invention correspond to formula I wherein $R_1$ and $R_2$ are methoxy; $R_3$ is hydrogen or methyl; $R_4$ is ethyl; and $R_5$ and $R_6$ are methoxyethyl.

The compounds of formula I and their salts contain at least one centre of chirality, i.e. at the α-carbon atom, and exist therefore as stereoisomers, including enantiomers and, when appropriate, diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the racemic mixtures containing substantially equal amounts or the two enantiomers.

Preferred are the α-amino acid phenyl ester derivatives of formula I wherein the configuration at the α-carbon atom is that of the R-enantiomer. Particular preferred compounds according to the invention, which have found to be useful as hypnotics for intravenous anaesthesia, are:

R-2-[N-bis(2-methoxyethyl)amino]butyric acid 2,6-dimethoxy-4-methylphenyl ester;
R-2-[N-bis(2-methoxyethyl)amino]butyric acid, 2,6-dimethoxyphenyl ester; and pharmaceutically acceptable salts thereof.

γ-Aminobutyric acid (GABA) is the major inhibitory neurotransmitter within the central nervous system and it is probable that compounds potentiating the effects of GABA at $GABA_A$ receptors will induce anaesthesia (S. A. Zimmerman, M. V. Jones and N. L. Harrison, J. Pharmacol. Exp. Therap. 1994, 270, 987–991; N. P. Franks and W. R. Lieb, Nature 1994, 367, 607–614). Indeed there is compelling evidence that many hypnotics exert their biological activity via modulation of $GABA_A$ receptors, including steroids, barbiturates, benzodiazepines and propofol (D. L. Tanelian, P. Kosek, I. Mody and M. B. MacIver, Anesthesiology 1993, 78, 757–776). The compounds of the present invention have been shown to allosterically modulate $GABA_A$ receptors by inhibiting the specific binding of the radioligand [$^{35}$S]-tert-butyl bicyclophosphorothionate to rat whole brain membranes. The in vitro results presented in Table 1 demonstrate modulation of GABAergic function by the compounds of the present invention and suggest this mechanism mediates or enhances their hypnotic activity.

In addition to their general anaesthetic activity, the compounds of the invention can be used as sedative and analgesic drugs and in the treatment of GABA related diseases, such as anxiety (e.g. panic attack), stress, sleep disorders, post natal depression, and premenstrual tension, and in the alleviation of seizure.

The invention also relates to pharmaceutical compositions comprising an α-amino acid phenyl ester derivative having the general formula I or a pharmaceutically acceptable salt thereof.

The compounds of the invention may be prepared by condensation of an appropriately $R_1,R_2,R_3$-substituted phenol, wherein $R_1$, $R_2$ and $R_3$ have the previously given meanings, with an acid halogenide according to the formula $Hal_1$-$CHR_4$—CO-$Hal_2$, wherein $R_4$ has the meaning as previously defined and $Hal_1$ and $Hal_2$ are independently iodo, bromo or chloro, preferably bromo, after which the resulting intermediate ester derivative of formula II

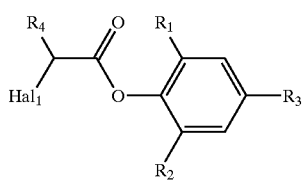

Formula II is reacted with an amine according to the formula $R_5R_6NH$, wherein $R_5$ and $R_6$ have the meanings as previously defined, optionally followed by conversion into a pharmaceutically acceptable salt.

The acid halogenide according to the formula $Hal_1$-$CHR_4$—CO-$Hal_2$ may be prepared from the α-halogeno acid $Hal_1$-$CHR_4$—COOH by treatment with an inorganic acid halide, such as thionyl chloride, or an organic acid halide, such as oxalyl chloride. The intermediate α-halogeno acid $Hal_1$-$CHR_4$—COOH can be prepared using methods well known to the skilled person, for example by treatment of the corresponding α-amino acid, $NH_2$—$CR_4$—COOH with sodium nitrite in aqueous hydrobromic acid.

Alternatively the intermediate ester derivative of formula II may be prepared by condensation of an appropriately $R_1,R_2,R_3$-substituted phenol, wherein $R_1$, $R_2$ and $R_3$ have the previously given meanings, with an acid according to the formula $Hal_1$-$CHR_4$—$CO_2H$, wherein $R_4$ has the meaning as previously defined and $Hal_1$ is iodo, bromo or chloro, preferably bromo, with the aid of a condensing agent, such as bromo-trispyrrolidino-phosphonium hexafluorophosphate (PyBrop), dicyclohexyl-carbodiimide/N-hydroxybenzotriazole and the like.

The compounds of the invention may also be prepared by condensation of an appropriately $R_1,R_2,R_3$-substituted phenol, wherein $R_1$, $R_2$ and $R_3$ have the previously given meanings, with an α-amino acid derivative according to the formula $R_5R_6N$—$CHR_4$—$CO_2H$, wherein $R_4$, $R_5$ and $R_6$ have the previously given meanings, with the use of a condensation agent, such as those mentioned above.

The α-amino acid phenyl ester derivatives of Formula I contain at least one chiral carbon atom, i.e. the α-carbon atom. The compounds can therefore be obtained as pure stereoisomers, or as a mixture of stereoisomers. Methods for asymmetric synthesis whereby the pure stereoisomers are obtained are well known in the art, e.g. synthesis with chiral induction, enantioselective enzymatic ester hydrolysis, separation of stereoisomers or enantiomers using chromatography on chiral media. Such methods are for example described in *Chirality in Industry* (edited by A. N. Collins, G. N. Sheldrake and J. Crosby, 1992; John Wiley).

Pharmaceutically acceptable salts may be obtained by treating the free base of the compounds according to formula I with a mineral acid such as hydrochloric acid, hydrobromic acid, phosphoric acid, and sulphuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulphonic acid and the like.

The present invention further provides pharmaceutical compositions comprising an α-amino acid phenyl ester derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use. Mixed with such pharmaceutically acceptable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray. For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol. The invention further includes a pharmaceutical composition, as hereinbefore described, in combination with packaging material suitable for said composition, said packaging material including instructions for the use of the composition for the use as hereinbefore described. The compounds of the invention may be administered for humans in a dosage of 0.001–50 mg per kg body weight, preferably in a dosage of 0.1–20 mg per kg body weight.

The invention is illustrated by the following examples.

EXAMPLES

General

Analysis of Compounds: The mass spectra of compounds of Formula I and their salts by electron spray ionisation (ESI) afford a parent ion that corresponds to the mass of the free base. While either the compound of Formula I or its salt may have been analysed by this method, the result is indicated below for the compound (and not the salt) in the following examples.

Example 1

1a: (±)-2-bromobutyric acid, 2,6-dimethoxy-4-methylphenyl ester

2-Bromobutyryl bromide (31.1 ml) was added to a stirred solution of 2,6-dimethoxy-4-methylphenol (45 g) in dry dichloromethane (500 ml), whereupon triethylamine (37.3 ml) was added dropwise over 30 minutes, maintaining the internal temperature below 10° C. using an ice-salt bath. During the addition a white precipitate formed. After addition was complete the reaction mixture was stirred for 1.5 hours, then filtered. The solid was washed with diethyl ether (200 ml) and the filtrate washed twice with saturated sodium bicarbonate solution (100 ml). The organic phase was dried over magnesium sulphate, filtered and the solvent removed under reduced pressure to give the crude product as an oil (79.4 g). To remove any residual starting phenol, the oil was dissolved in diethyl ether and washed with sodium hydroxide solution (0.1 M; 3×100 ml), then water (4×100 ml). The organic phase was dried over magnesium sulphate, filtered and the solvent removed under reduced pressure to give the title compound as a yellow oil (72.9 g).

$^1$H NMR (CDCl$_3$); δ1.15 (t, 3H), 2.05–2.35 (m, 2H), 2.34 (s, 3H), 3.80 (s, 6H), 4.45 (t, 1H), 6.40 (s, 2H).

The following intermediate compounds 1b–1h according to Formula II were prepared in a similar manner: In some instances the starting bromo acid was not commercially available and was synthesized as described in the text.

1b: (±)-2-bromobutyric acid, 2,6-dimethoxyphenyl ester $^1$H NMR (CDCl$_3$); δ1.15 (t, 3H), 2.10–2.35 (m, 2H), 3.82 (s, 6H), 4.47 (t, 1H), 6.60 (d, 2H), 7.15 (t, 1H).

1c: (±)-2-bromopropionic acid, 2,6-dimethoxy-4-methylphenyl ester $^1$H NMR (CDCl$_3$); δ1.97 (d, 3H), 2.35 (s, 3H), 3.80 (s, 6H), 4.68 (q, 1H), 6.42 (s, 2H).

1d: (±)-2-bromopropionic acid, 2,6-dimethoxyphenyl ester $^1$H NMR (CDCl$_3$); δ1.98 (d, 3H), 3.80 (s, 3H), 4.68 (q, 1H), 6.61 (d, 2H), 7.14 (t, 1H).

1e: (±)-2-bromohexanoic acid, 2,6-dimethoxyphenyl ester $^1$H NMR (CDCl$_3$); δ7.13 (t, 1H), 6.61 (d, 2H), 4.52 (t, 1H), 3.81 (s, 6H), 2.25 (m, 1H), 2.23 (m, 1H), 1.54 (m, 2H), 1.40 (m, 2H), 0.95 (t, 3H).

1f: (±)-2-bromohexanoic acid, 2,6-dimethoxy-4-methylphenyl ester $^1$H NMR (CDCl$_3$): δ0.95 (t, 3H), 1.34–1.65 (m, 4H), 2.05–2.30 (m, 4H), 2.33 (s, 3H), 3.79 (s, 6H), 4.48 (t, 1H), 6.41 (s, 2H).

1g: (±)-2-bromopentanoic acid, 2,6-dimethoxy-4-methylphenyl ester $^1$H NMR (CDCl$_3$): δ0.86–1.04 (3H), 1.13–1.26 (2H), 1.87–2.27 (2H), 2.33 (3H), 3.78 (6H), 4.45–4.56 (1H), 6.41 (2H).

1h: 2-bromo-4-methylpentanoic acid, 2,6-dimethoxyphenyl ester $^1$H NMR (CDCl$_3$); δ0.98 (d, 3H), 1.02 (d, 3H), 1.90–2.04 (m, 2H), 2.10–2.17 (m, 1H), 3.81 (s, 6H), 4.50 (t, 1H), 6.61 (d, 2H), 6.11 (t, 1H).

1i: 2-bromo-4-methylpentanoic acid, 2,6-dimethoxy-4-methylphenyl ester

A solution of sodium nitrite (31.55 g) in water (70 ml) was added dropwise to a stirred solution of D-leucine (20 g) in 47% aqueous hydrobromic acid (140 ml)/water (211 ml) at 0° C. The reaction mixture was allowed to warm to room temperature and stirred for 20 hours, then diluted with diethyl ether (600 ml). The organic layer was separated and washed with aqueous sodium metabisulphite (200 ml), dried over sodium sulphate, filtered and the solvent removed under reduced pressure to give 2-bromo-4-methyl-pentanoic acid as a yellow oil (27.6 g) [$^1$H NMR (CDCl$_3$): δ0.93 (d, 3H), 0.98 (d, 3H), 1.75–1.85 (m, 1H), 1.91–1.95 (m, 2H), 4.30 (t, 1H)]. Oxalyl chloride (9.56 ml) was added dropwise to a stirred solution of the 2-bromo-4-methylpentanoic acid (10.7 g) and pyridine (0.1 ml) in dichloromethane (60 ml). The reaction mixture was stirred for 20 hours and the solvent was removed under reduced pressure to give 2-bromo-4-methylpentanoyl chloride (12 g) [$^1$H NMR (CDCl$_3$); δ0.95 (d, 3H), 1.01 (d, 3H), 1.80–2.07 (m, 3H), 4.52 (t, 1H)]. A solution of this 2-bromo-4-methylpentanoyl chloride (12 g) in dichloromethane (40 ml) was added dropwise to a stirred solution of 2,6-dimethoxy-4-methylphenol (9.41 g) and triethylamine (15.6 ml) in dichloromethane (20 ml). The reaction mixture was stirred for 20 hours and was then chromatographed on silica gel, eluting with dichloromethane, to give the title compound as a viscous yellow oil (14.7 g).

$^1$H NMR (CDCl$_3$); δ0.97 (d, 3H), 1.01 (d, 3H), 1.90–2.13 (m, 3H), 2.34 (s, 3H), 3.79 (s, 6H), 4.53 (t, 1H), 6.41 (s, 2H).

1j: 2-bromo-3-methylbutyric acid, 2,6-dimethoxy-4-methylphenyl ester

Using the same method as described for Example 1i, but starting from DL-valine, the title compound was obtained as an orange solid (77.3 g).

$^1$H NMR (CDCl$_3$); δ1.17–1.19 (m, 6H), 3.33 (s, 3H), 2.38–2.47 (m, 1H), 3.79 (s, 6H), 4.36 (d, 1H), 6.41 (s, 2H).

Example 2 a: S-2-bromopropionic acid, 2,6-dimethoxyphenyl ester

A solution of S-(−)-2-bromopropionic acid (58.8 g) in dry dichloromethane (590 ml) was stirred at room temperature. Oxalyl chloride (73 ml) and dichloromethane (70 ml) were added, after which gas evolution was observed. After 28 hours the solution was concentrated under reduced pressure and purged with dichloromethane (2×150 ml). Concentration of this solution (600 mmHg, 40° C.) gave a mixture of S-2-bromopropionyl chloride in dichloromethane [103 g, comprising S-2-bromopropionyl chloride (~76 g) and dichloromethane (~27 g)].

$^1$H NMR (CDCl$_3$): δ1.92 (d, 3H), 4.65 (q, 1H).

A solution of S-2-bromopropionyl chloride (66 g) and 2,6-dimethoxyphenol (55 g) in dry toluene was stirred under nitrogen and cooled to −10° C. A solution of dry pyridine (32.2 ml) in dry toluene (60 ml) was added dropwise keeping the temperature below 0° C. After 20 minutes the resulting suspension was diluted with water (500 ml) and the mixture filtered through a dicalite pad to remove a small amount of white solid. The dicalite pad was rinsed with toluene (400 ml) and the filtrate was washed with water (3×150 ml) then dried over magnesium sulphate and filtered. The solution was concentrated under reduced pressure and purged with toluene to give S-2-bromopropionic acid, 2,6-dimethoxyphenyl ester (92.6 g) as a straw coloured oil which solidified on cooling. This material was sufficiently pure for use in subsequent steps. $^1$H NMR and chiral analytical chromatography on a Chiracel OJ column using hexane-isopropanol (9:1) as the eluent showed the product mixture comprised S-2-bromopropionic acid, 2,6-dimethoxyphenyl ester (91.3%), R-2-bromopropionic acid, 2,6-dimethoxyphenyl ester (4.8%) and R-2-chloropropionic acid, 2,6-dimethoxyphenyl ester (3.8%).

$^1$H NMR (CDCl$_3$): δ1.98 (d, 3H), 3.82 (s, 3H), 4.70 (q, 1H), 6.65 (d, 2H), 7.15 (t, 1H).

The following compound was prepared in a similar manner:

2b: S-2-bromopropionic acid, 2,6-dimethoxy-4-methylphenyl ester $^1$H NMR (CDCl$_3$): δ1.96 (d, 3H), 2.34 (s, 3H), 3.80 (s, 6H), 4.68 (q, 1H), 6.42 (s 2H).

Example 3

3a: (±)-2-[N-bis(2-methoxyethyl)amino]butyric acid, 2,6-dimethoxy-4-methylphenyl ester A solution of 2-bromobutyric acid, 2,6-dimethoxy-4-methylphenyl ester (64.7 g) in dry toluene (328 ml) was heated to reflux with stirring, whereupon dry triethylamine (4×31.2 ml) and bis(2-methoxyethyl)amine (4×32.9 ml) were added as aliquots over 48 hours. The reaction mixture was allowed to cool, then filtered and the solid was washed with diethyl ether. The filtrate was concentrated under reduced pressure to low volume, then diluted with water (500 ml) and extracted with diethyln ether (3×350 ml). The combined extracts were washed with water (2×350 ml), then extracted with aqueous hydrochloric acid (1 M; 3×350 ml). The combined acidic extracts were cooled in ice-water and basified to ph 10 with sodium hyudroxide solution (4M; 225 ml). The resulting solution was extracted with diethyl ether (33×500 ml) and the combined extracts washed with water (2×500 ml). The organic phase was dried over magnesium sulphate, filtered and the solvent removed under reduced pressure to give the crude product as an oil (50.5 g). Chromatography of this oil on silica gel and removal of any residual starting phenol as described above afforded the racemic title compound as a yellow oil (46.6 g).

$^1$H NMR (CDCl$_3$); δ1.05 (t, 3H), 1.65–1.8 (m, 1H), 1.9–2.05 (m, 1H), 2.35 (s, 3H), 2.85–3.1 (m, 4H), 3.36 (s, 6H), 3.4–3.5 (m, 4H), 3.55 (t, 1H), 3.77 (s, 6H), 6.40 (s, 2H). Positive ion ESI (M+H)$^+$370.

The following compounds were prepared in a similar manner. In some instances reactions were carried out in the absence of solvent and in others acetone was used instead of toulune as the reaction solvent and diisopropylethylamine was used instead of triethylamine as a base. In some cases the starting amine was not commercially available and was synthesized as described in the text. In several instances crude product mixtures were purified by chromatography on alumina rather than silica gel. Racemates are denoted (±), enantiomers (≧95% ee, resolved via chiral hplc or enzymatic methodology) are denoted by absolute stereochemistry i.e. R or S and/or optical rotation i.e. (+) or (−), while eneantiormeric mixtures (≦97% ee, prepared from the above S-bromo phenolic esters) have no stereochemistry assigned, i.e. there is no (+), (−), (+/−), R or S prior to the chemical name (e.g. example 7i).

3b: (±)-2-[N-bis(2-methoxyethyl)amino]buytric acid, 2,6-dimethoxyphenyl ester $^1$H NMR (CDCl$_3$); δ1.05 (t, 3H), 1.65–2.05 (m, 2H), 2.8–3.15 (m, 4H), 3.3–3.65 (m, 5H), 3.36 (s, 6H), 3.80 (s, 6H), 6.6 (d, 2H), 7.15 (t, 1H).

3c: (±)-2-[N-bis(2-ethoxyethyl)amino]propionic acid, 2,6-dimethoxyphenyl ester $^1$H NMR (CDCl$_3$); δ1.20 (t, 6H), 1.48 (d, 3H), 2.8–3.1 (m, 4H), 3.45–3.65 (m, 8H), 3.80 (s, 6H), 3.90 (q, 1H), 6.6 (d, 2H), 7.1 (t, 1H). IR (thin film): 1758, 1607, 1482, 1304, 1260, 1115 cm$^{-1}$. Positive ion ESI (M+H)$^+$370.

3d: (±)-2-[N-bis(2-methoxyethyl)amino]propionic acid, 2,6-dimethoxy-4-methylphenyl ester $^1$H NMR (CDCl$_3$); δ1.5 (d, 3H), 2.35 (s, 3H), 2.85–3.15 (m, 4H), 3.35 (s, 6H), 3.4–3.55 (m, 4H), 3.8 (s, 6H), 3.9 (q, 1H), 6.4 (s, 2H).

3e: (±)-2-[N-bis(2-methoxyethyl)amino]propionic acid, 2,6-dimethoxyphenyl ester $^1$H NMR (CDCl$_3$); δ1.50 (d, 3H), 2.85–3.15 (m, 4H), 3.36 (s, 6H), 3.4–3.6 (m, 4H), 3.80 (s, 6H), 3.90 (q, 1H), 6.6 (d, 2H), 7.1 (t, 1H). 3f: (±)-2-[N-methylbenzylamino]propionic acid, 2,6-dimethoxy-4-methylphenyl ester Positive ion ESI (M+H)$^+$344.

3g: 2-[N-methylbenzylamino]propionic acid, 2,6-dimethoxy-4-methylphenyl ester

Positive ion ESI (M+H)$^+$344.

3h: 2-[N-methylallylamino]propionic acid, 2,6-dimethoxy-4-methylphenyl ester

Positive ion ESI (M+H)$^+$294.

3i: (±)-2-[diethylamino]propionic acid, 2,6-dimethoxy-4-methylphenyl ester

Positive ion ESI (M+H)$^+$296.

3j: (±)-2-[N-methylbenzylamino]buytric acid, 2,6-dimethoxyphenyl ester $^1$H NMR (CDCl$_3$); δ1.1 (t, 3H), 1.75–2.1 (m, 2H), 2.40 (s, 3H), 3.55 (t, 1H), 3.7–4.0 (m, 2H), 3.83 (s, 6H), 6.65 (d, 2H), 7.1–7.45 (m, 6H). Positive ion ESI (M+H)$^+$344.

3k: (±)-2-[N-bis(2-ethoxyethyl)amino]butyric acid, 2,6-dimethoxyphenyl ester
Positive ion ESI (M+H)$^+$384.

3l: 2-[N-methylphenethylamino]propionic acid, 2,6-dimethoxyphenyl ester
Positive ion ESI (M+H)$^+$344.

3m: (±)-2-[N-bis(2-methoxyethyl)amino]butyric acid, 2,6-diethoxyphenyl ester
Positive ion ESI (M+H)$^+$384.

3n: (±)-2-[N-bis(2-methoxyethyl)amino]butyric acid, 2,6-di-(1-methyl)ethoxyphenyl ester
Positive ion ESI (M+H)$^+$412.

3o: 2-[N-methyl-(2-methoxy)ethylamino]propionic acid, 2,6dimethoxyphenyl ester
Positive ion ESI (M+H)$^+$312.

3p: (±)-2-[N-bis(2-methoxycarboylethyl)amino]butyric acid, 2,6-dimethoxyphenyl ester
Positive ion ESI (M+H)$^+$412.

3q: (±)-2-[N-(2-ethoxycarbonylethyl)amino-N-(2-methoxycarbonylethyl)amino]butyric acid, 2,6-dimethoxyphenyl ester
Positive ion ESI (M+H)$^+$426.

3r: (±)-2-[N-bis(2-methoxyethyl)amino]hexanoic acid, 2,6-dimethoxyphenyl ester
Positive ion ESI (M+H)$^+$384.

3s: (±)-2-[N-bis(2-methoxyethyl)amino]pentanoic acid, 2,6-dimethoxy-4-methyl-phenyl ester
Positive ion ESI (M+H)$^+$384.

3t: (±)-2-[N-bis(2-methoxyethyl)amino]hexanoic acid, 2,6-dimethoxy-4-methylphenyl ester
Positive ion ESI (M+H)$^+$398.

3u: (±)-2-[N-bis(2-methoxypropyl)amino]butyric acid, 2,6-dimethoxyphenyl ester
Positive ion ESI (M+H)$^+$384.

3v: (±)-2-[N-bis(2-methoxyethyl)amino]hexanoic acid, 2,6-dimethoxy-4-methylphenyl ester.

2-Bromohexanoic acid, 2,6-dimethoxy-4-methylphenyl ester (14.5 g) and bis(2-methoxyethyl)amine (16.4 ml) were heated at 100 ° C. for 3 hours and the mixture then allowed to cool to room temperature. The mixture was diluted with diethyl ether (200 ml) and washed with water and dilute hydrochloric acid. The acidic fraction was basified using sodium carbonate and extracted with diethyl ether. The organic phase was dried over sodium sulphate, filtered and concentrated under reduced pressure to give an oil. Chromatography of this oil on silica gel with diethyl ether-petroleum ether (2:3 v/v) as the eluent afforded the title compound as an oil (8.7 g).

$^1$H NMR (CDCl$_3$); δ0.94 (t, 3H), 1.31–1.58 (m, 4H), 1.65–1.77 (m, 1H), 1.84–1.97 (m, 1H), 2.32 (s, 3H), 2.86–3.08 (m, 4H), 3.35 (s, 6H), 3.40–3.54 (m, 4H), 3.63 (t, 1H), 3.76 (s, 6H), 6.39 (s, 2H). Positive ion ESI (M+H)$^+$398.

The following compounds 3w–3z and 3aa were prepared in a manner similar to that described for Example 3v:

3w: (±)-2-[N-bis(2-methoxyethyl)amino]-4-methylpentanoic acid, 2,6-dimethoxy-4-methylphenylester
Positive ion ESI (M+H)$^+$398.

3x: (±)-2-[N-(2-methoxyethyl)-N-methylamino]-4-methylpentanoic acid, 2,6dimethoxy-4-methylphenylester
Positive ion ESI (M+H)$^+$354.

3y: (±)-2-[N-bis(2-methoxyethyl)amino]-3-methylbutyric acid, 2,6-dimethoxy-4-methylphenylester
Positive ion ESI (M+H)$^+$384.

3z: (±)-2-[N-bis(2-methoxyethyl)amino]-4-methylpentanoic acid, 2,6-dimethoxyphenylester
Positive ion ESI (M+H)$^+$384.

3aa: (±)-2-[N-(2-methoxyethyl)-N-methylamino]-4-methylpentanoic acid, 2,6-dimethoxyphenylester
Positive ion ESI (M+H)$^+$340.

Example 4

4a: (±)-2-[N-bis(2-methoxyethyl)amino]pentanoic acid, 2,6-dimethoxyphenyl ester

To a stirred solution of (±)-2-[N-bis(2-methoxyethyl)amino]pentanoic acid hydrochloride (1:1) salt (14 g) in dimethylformamide (280 ml) was added triethylamine (7.3 ml). After 30 minutes 1-(3-dimethylaminopropyl)-3-ethylcarbodiimide hydrochloride (12.92 g) was added. After a further 30 minutes 2,6-dimethoxyphenol (7.99 g) and N,N-dimethylaminopyridine (189 mg) were added and stirring continued for 3 days. The reaction mixture was poured into water, extracted with dichloromethane and the combined extracts washed with dilute hydrochloric acid, dried over sodium sulphate, filtered and the solvent removed under reduced pressure to give the crude product as an oil (10.24 g). Chromatography of this oil on alumina afforded the racemic title compound as an oil (1.48 g).

$^1$H NMR (CDCl$_3$); δ1.0 (t, 3H), 1.45–1.6 (m, 2H), 1.65–1.75 (m, 1H), 1.85–1.95 (m, 1H), 2.9–3.1 (m, 4H), 3.36 (s, 6H), 3.4–3.6 (m, 4H), 3.7 (t, 1H), 3.80 (s, 6H), 6.6 (d, 2H), 7.1 (t, 1H). Positive ion ESI (M+H)$^+$344.

The following compounds were prepared in a similar manner:

4b: (±)-2-[N-bis(2-methoxyethyl)amino]butyric acid, 2,4,6-trimethoxyphenyl ester
Positive ion ESI (M+H)$^+$386.

4c: (±)-3-methyl-2-[N-bis(2-methoxyethyl)amino]butyric acid, 2,6-dimethoxyphenyl ester
Positive ion ESI (M+H)$^+$370.

Example 5

5a: R-(+)-2-[N-bis(2-methoxyethyl)amino]butyric acid, 2,6-dimethoxy-4-methylphenyl ester The racemic 2-[N-bis(2-methoxyethyl)amino]butyric acid, 2,6-dimethoxy-4-methylphenyl ester, described previously, was resolved via chiral preparative chromatography on a Chiracel OJ column (2 cm×25 cm; Daicel) using hexane-isopropanol-diethylamine (95:5:0.1 v/v/v) as the eluent. The title compound with R absolute configuration eluted first; [α]$_D$=+43.3° (c=0.6 in chloroform).

The following compounds were prepared in a similar manner:

5b: S-(-)-2-[N-bis(2-methoxyethyl)amino]butyric acid, 2,6-dimethoxy-4-methylphenyl ester
Positive ion ESI (M+H)$^+$370.

5c: R-2-[N-bis(2-ethoxyethyl)amino]propionic acid, 2,6-dimethoxyphenyl ester
Positive ion ESI (M+H)$^+$370.

5d: S-2-[N-bis(2-ethoxyethyl)amino]propionic acid, 2,6-dimethoxyphenyl ester
Positive ion ESI (M+H)$^+$370.

5e: R-2-[N-bis(2-methoxyethyl)amino]propionic acid, 2,6-dimethoxy-4-methyl phenyl ester
Positive ion ESI (M+H)$^+$356.

5f: R-2-[N-bis(2-ethoxyethyl)amino]butyric acid, 2,6-dimethoxyphenyl ester

Positive ion ESI (M+H)⁺384.

5g: S-2-[N-bis(2-ethoxyethyl)amino]butyric acid, 2,6-dimethoxyphenyl ester

Positive ion ESI (M+H)⁺384.

5h: 2-[N-bis(2-methoxyethyl)amino]hexanoic acid, 2,6-dimethoxyphenyl ester

Both enantiomers (>95% ee) were prepared; each showed the positive ion ESI (M+H)⁺384.

Example 6

6a: R-2-[N-bis(2-methoxyethyl)amino]butyric acid, 2,6-dimethoxyphenyl ester (±)-2-[N-bis(2-methoxyethyl)amino]butyric acid, 2,6-dimethoxyphenyl ester (40.0 g) was dissolved in phosphate buffer (1066 mL; prepared with disodium hydrogen phosphate (17.32 g) and sodium dihydrogen phosphate dihydrate (12.17 g) per litre of water and the pH adjusted to 7.0 with 2M sodium hydroxide solution). Porcine liver esterase (5.27 g, 19 units/mg solid, Sigma cat. no. E3019) was added to this mixture, which was stirred for 4 days at room temperature. Methyl t-butyl ether (1 l) was then added and the mixture stirred overnight. The layers were separated and the aqueous phase extracted again with methyl t-butyl ether (1 l). The combined organic liquors were dried over sodium sulphate, filtered and the solvent removed under reduced pressure to give the crude product as an oil (20.5 g). Chromatography of this oil on alumina using petroleum ether-ethyl acetate (7:3 v/v) as the eluent afforded the title compound as an oil (10.14 g).

Positive ion ESI (M+H)⁺356.

The following compound was prepared in a similar manner:

6b: R-2-[N-bis(2-methoxyethyl)amino]pentanoic acid, 2,6-dimethoxyphenyl ester

Positive ion ESI (M+H)⁺370.

Example 7

7a: R-(+)-2-[N-bis(2-methoxyethyl)amino]butyric acid, 2,6-dimethoxy-4-methylphenyl ester hydrochloride (1:1) salt Hydrogen chloride gas was passed through a solution of 2R-[N-bis(2-methoxyethyl)amino]butyric acid, 2,6-dimethoxy-4-methylphenyl ester (16.5 g) in diethylether (175 ml) for 2–3 minutes, after which precipitation of the salt was deemed complete. The solvent was removed under reduced pressure to give a gummy solid which was suspended in a mixture of diethyl ether (120 ml) and dichloromethane (20 ml). This mixture was stirred rapidly and cooled using an ice bath. The resulting white solid that precipitated was filtered off and washed with diethyl ether to give the title compound (14.5 g).

¹H NMR (CDCl₃+C₅D₅N); δ1.13 (t, 3H), 1.95–2.1 (m, 2H), 2.34 (s, 3H), 3.05–3.35 (m, 4H), 3.37 (s, 6H), 3.55–3.75 (m, 4H), 3.78 (s, 6H), 3.85 (t, 1H), 6.3 (br, NH⁺), 6.40 (s, 2H). IR (KBr disc): 3416, 1768, 1606, 1506, 1465 cm⁻¹.

[α]$_D$=+7.03° (c=0.8 in chloroform).

The following compounds were prepared in a similar manner. In some cases the salt was prepared and isolated without dichloromethane.

7b: (±)-2-[N-bis(2-methoxyethyl)amino]butyric acid, 2,6-dimethoxy-4-methylphenyl ester hydrochloride (1:1) salt ¹H NMR (CDCl₃+C₅D₅N); δ1.31 (t, 3H), 1.95–2.15 (m, 2H), 2.34 (s, 3H), 3.1–3.35 (m, 4H), 3.37 (s, 6H), 3.55–3.65 (m, 2H), 3.7–3.8 (m, 2H), 3.78 (s, 6H), 3.85 (q, 1H), 6.42 (s, 2H), 6.9 (br, NH⁺). IR (KBr disc): 1768, 1607, 1508, 1470, 1412 cm⁻¹.

7c: (±)-2-[N-bis(2-methoxyethyl)amino]butyric acid, 2,6-dimethoxyphenyl ester hydrochloride (1:1) salt ¹H NMR (CDCl₃+C₅D₅N); δ1.13 (t, 3H), 1.95–2.05 (m, 2H), 3.05–3.3 (m, 4H), 3.38 (s, 6H), 3.55–3.75 (m, 4H), 3.80 (s, 6H), 3.85 (t, 1H), 5.65 (br, NH⁺), 6.6 (d, 2H), 7.14 (t, 1H).

7d: (±)-2-[N-bis(2-ethoxyethyl)amino]propionic acid, 2,6-dimethoxyphenyl ester hydrochloride (1:1) salt ¹H NMR (CDCl₃+C₅D5N); δ1.21 (t, 6H), 1.71 (d, 3H), 3.2–3.4 (m, 4H), 3.5–3.6 (m, 4H), 3.6–3.75 (m, 2H), 3.80 (s, 6H), 3.8–3.9 (m, 2H), 4.35 (q, 1H), 5.9 (br, NH⁺), 6.60 (d, 2H), 7.15 (t, 1H). IR (KBr disc): 1768, 1606, 1585, 1484, 1454 cm⁻¹.

7e: (±)-2-[N-bis(2-methoxyethyl)amino]propionic acid, 2,6-dimethoxy-4-methylphenyl ester hydrochloride (1:1) salt M.p. 96–97° C; ¹H NMR (CDCl₃+C₅D₅N); δ1.67 (d, 3H), 2.33 (s, 3H), 3.15–3.35 (m, 4H), 3.37 (s, 6H), 3.55–3.65 (m, 2H), 3.7–3.85 (m, 2H), 3.77 (s, 6H), 4.25 (q, 1H), 6.41 (s, 2H), 6.7 (br, NH⁺).

7f: (±)-2-[N-bis(2-methoxyethyl)amino]propionic acid, 2,6-dimethoxyphenyl ester hydrochloride (1:1) salt M.p. 114–116° C.; ¹H NMR (CDCl₃+C₅D₅N); δ1.69 (d, 3H), 3.15–3.35 (m, 4H), 3.38 (s, 6H), 3.55–3.65 (m, 2H), 3.7–3.85 (m, 2H), 3.80 (s, 6H), 4.25 (q, 1H), 6.5 (br, NH⁺), 6.60 (d, 2H), 7.14 (t, 1H).

7g: (±)-2-[N-methylbenzylamino]propionic acid, 2,6-dimethoxy-4-methylphenyl ester hydrochloride (1:1) salt ¹H NMR (CDCl₃+C₅D₅N); δ1.80 (d, 3H), 2.37 (s, 3H), 2.81 (s, 3H), 3.82 (s, 6H), 4.10 (q, 1H), 4.2–4.4 (m, 2H), 6.45 (s, 2H), 7.35–7.45 (m, 3H), 7.65–7.75 (m, 2H).

7h: R-(+)-2-[N-methylbenzylamino]propionic acid, 2,6-dimethoxy-4-methylphenyl ester hydrochloride (1:1) salt ¹H NMR (CDCl₃+C₅D₅N); δ1.80 (d, 3H), 2.37 (s, 3H), 2.81 (s, 3H), 3.82 (s, 6H), 4.10 (q, 1H), 4.2–4.4 (m, 2H), 6.45 (s, 2H), 7.35–7.45 (m, 3H), 7.65–7.75 (m, 2H). [α]$_D$=+67.8° (c=0.8 in chloroform)

7i: 2-[N-methylallylamino]propionic acid, 2,6-dimethoxy-4-methylphenyl ester hydrochloride (1:1) salt ¹H NMR (CDCl₃+C₅D₅N); δ1.88 (d, 3H), 2.36 (s, 3H), 2.89 (s, 3H), 3.75–3.90 (m, 2H), 3.80 (s, 6H), 4.35 (q, 1H), 5.45–5.55 (m, 2H) 6.25–6.40 (m, 1H), 6.45 (s, 2H).

7j: (±)-2-[diethylamino]propionic acid, 2,6-dimethoxy-4-methylphenyl ester hydrochloride (1:1) salt ¹H NMR (CDCl₃+C₅D₅N); δ1.52 (t, 6H), 1.92 (d, 3H), 2.35 (s, 3H), 3.15–3.30 (m, 2H), 3.45–3.60 (m, 2H), 3.78 (s, 6H), 4.45 (q, 1H), 6.40 (s, 2H).

7k: (±)-2-[N-methylbenzylamino]butyric acid, 2,6-dimethoxyphenyl ester hydrochloride (1:1) salt ¹H NMR (CDCl₃+C₅D₅N); δ1.16 (t, 3H), 2.00–2.15 (m, 1H), 2.20–2.35 (m, 1H), 2.71 (s, 3H), 3.8–3.9 (m, 1H), 3.85 (s, 6H), 4.15–4.35 (m, 2H), 5.2 (br, NH⁺), 6.65 (d, 2H), 7.2 (t, 1H), 7.3–7.45 (m, 3H), 7.6–7.7 (m, 2H).

7l: (±)-2-[N-bis(2-ethoxyethyl)amino]butyric acid, 2,6-dimethoxyphenyl ester hydrochloride (1:1) salt ¹H NMR (CDCl₃+C₅D₅N); δ1.12 (t, 3H), 1.20 (t, 6H), 1.95–2.10 (m, 2H), 3.1–3.3 (m, 4H), 3.52 (q, 4H), 3.55–3.75 (m, 4H), 3.80 (s, 6H), 3.85 (t, 1H), 6.60 (d, 2H), 7.13 (t, 1H), 7.4 (br, NH⁺).

7m: 2-[N-methylphenethylamino]propionic acid, 2,6-dimethoxyphenyl ester hydrochloride (1:1) salt ¹H NMR (CDCl₃+C₅D₅N); δ1.87 (d, 3H), 2.94 (s, 3H), 3.2–3.45 (m, 4H), 3.76 (s, 6H), 4.35 (q, 1H), 6.62 (d, 2H), 7.19 (t, 1H), 7.2–7.35 (m, 5H). [α]$_D$=3.3° (c=0.6 in chloroform)

7n: (±)-2-[N-bis(2-methoxyethyl)amino]butyric acid, 2,6-diethoxyphenyl ester hydrochloride (1:1) salt $^1$H NMR (CDCl$_3$+C$_5$D$_5$N); δ1.15 (t, 3H), 1.36 (t, 6H), 1.95–2.05 (m, 2H), 3.05–3.30 (m, 4H), 3.37 (s, 6H), 3.55–3.75 (m, 4H), 3.8 (m, 1H), 3.85–4.1 (m, 4H), 6.56 (d, 2H), 6.7 (br, NH$^+$), 7.1 (t, 1H).

7o: (±)-2-[N-bis(2-methoxyethyl)amino]butyric acid, 2,6-di-(1-methyl)ethoxyphenyl ester hydrochloride (1:1) salt $^1$H NMR (CDCl$_3$+C$_5$D$_5$N); δ1.14 (t, 3H), 1.20–1.35 (m, 12H), 1.95–2.05 (m, 2H), 3.05–3.30 (m, 4H), 3.37 (s, 6H), 3.5–3.7 (m, 4H), 3.8 (t, 1H), 4.45–4.60 (m, 2H), 5.7 (br, NH$^+$), 6.55 (d, 2H), 7.06 (t, 1H).

7p: 2-[N-methyl-(2-methoxy)ethylamino]propionic acid, 2,6-dimethoxyphenyl ester hydrochloride (1:1) salt $^1$H NMR (CDCl$_3$+C$_5$D$_5$N); δ1.83 (d, 3H), 2.35 (s, 3H), 2.93 (s, 3H), 3.33–3.45 (m, 2H), 3.40 (s, 3H), 3.79 (s, 6H), 3.8–4.0 (m, 2H), 4.35 (q, 1H), 6.43 (s, 2H).

[α]$_D$=+11.4° (c=0.6 in chloroform)

7q: (±)-2-[N-bis(2-methoxycarbonylethyl)amino]butyric acid, 2,6-dimethoxyphenyl ester hydrochloride (1:1) salt $^1$H NMR (CDCl$_3$+C$_5$D$_5$N); δ0.94 (t, 3H), 1.55–1.70 (m, 1H), 1.80–1.95 (m, 1H), 2.45 (t, 4H), 2.85–3.15 (m, 4H), 3.45 (t, 1H), 3.60 (s, 6H), 3.72 (s, 6H), 6.52 (d, 2H), 7.1 (t, 1H).

7r: (±)-2-[N-(2-ethoxycarbonylethyl)amino-N-(2-methoxycarbonylethyl)amino]butyric acid, 2,6-dimethoxyphenyl ester hydrochloride (1:1) salt $^1$H NMR (CDCl$_3$+C$_5$D$_5$N); δ1.01 (t, 3H), 1.26 (t, 3H), 1.65–1.80 (m, 1H), 1.90–2.05 (m, 1H), 2.45–2.55 (m, 4H), 2.95–3.20 (m, 4H), 3.55 (t, 1H), 3.67 (s, 3H), 3.80 (s, 6H), 4.15 (q, 2H), 6.59 (d, 2H), 7.1 (t, 1H).

7s: (±)-2-[N-bis(2-methoxyethyl)amino]pentanoic acid, 2,6-dimethoxyphenyl ester hydrochloride (1:1) salt $^1$H NMR (CDCl$_3$+C$_5$D$_5$N); δ1.0 (t, 3H), 1.5–1.65 (m, 2H), 1.85–2.0 (m, 2H), 3.05–3.3 (m, 4H), 3.37 (s, 6H), 3.5–3.7 (m, 4H), 3.80 (s, 6H), 3.9 (t, 1H), 6.6 (d, 2H), 7.13 (t, 1H), 7.2 (br, NH$^+$).

7t: (±)-2-[N-bis(2-methoxyethyl)amino]butyric acid, 2,4,6-trimethoxyphenyl ester hydrochloride (1:1) salt $^1$H NMR (CDCl$_3$+C$_5$D$_5$N); δ1.10 (t, 3H), 1.95–2.05 (m, 2H), 3.05–3.30 (m, 4H), 3.37 (s, 6H), 3.55–3.75 (m, 4H), 3.78 (s, 6H), 3.8 (m, 1H), 3.80 (s, 3H), 6.15 (s, 2H), 7.15 (br, NH$^+$).

7u: (±)-3-methyl-2-[N-bis(2-methoxyethyl)amino]butyric acid, 2,6-dimethoxyphenyl ester hydrochloride (1:1) salt $^1$H NMR (CDCl$_3$+C$_5$D$_5$N); δ1.0–1.1 (m, 6H), 2.05–2.2 (m, 1H), 2.85–3.10 (m, 4H), 3.20 (d, 1H), 3.36 (s, 6H), 3.40–3.55 (m, 4H), 3.79 (s, 6H), 6.4 (br, NH$^+$), 6.6 (d, 2H), 7.1 (t, 1H).

7v: S-(−)-2-[N-bis(2-methoxyethyl)amino]butyric acid, 2,6-dimethoxy-4-methylphenyl ester hydrochloride (1:1) salt $^1$H NMR (CDCl$_3$+C$_5$D$_5$N); δ1.13 (t, 3H), 1.95–2.1 (m, 2H), 2.33 (s, 3H), 3.05–3.35 (m, 4H), 3.36 (s, 6H), 3.55–3.75 (m, 4H), 3.75 (t, 1H), 3.77 (s, 6H), 5.2 (br, NH$^+$), 6.40 (s, 2H). [α]$_D$=−5.5° (c=0.7 in chloroform).

7w: (+)-2-[N-bis(2-ethoxyethyl)amino]propionic acid, 2,6-dimethoxyphenyl ester hydrochloride (1:1) salt $^1$H NMR (CDCl$_3$+C$_5$D$_5$N); δ1.21 (t, 6H), 1.75 (d, 3H), 3.3–3.45 (m, 4H), 3.35–3.6 (m, 4H), 3.65–3.75 (m, 2H), 3.80 (s, 6H), 3.85–4.0 (m, 2H), 4.4 (q, 1H), 6.60 (d, 2H), 6.8 (br, NH$^+$), 7.15 (t, 1H). [α]$_D$=+6.6° (c=0.6 in chloroform)

7x: (−)-2-[N-bis(2-ethoxyethyl)amino]propionic acid, 2,6-dimethoxyphenyl ester hydrochloride (1:1) salt $^1$H NMR (CDCl$_3$+C$_5$D$_5$N); δ1.23 (t, 6H), 1.78 (d, 3H), 3.3–3.45 (m, 4H), 3.5–3.6 (m, 4H), 3.65–3.75 (m, 2H), 3.82 (s, 6H), 3.85–4.0 (m, 2H), 4.45 (q, 1H), 6.65 (d, 2H), 6.7 (br, NH$^+$), 7.20 (t, 1H). [α]$_D$=−4.9° (c=0.7 in chloroform)

7y: R-(+)-2-[N-bis(2-methoxyethyl)amino]propionic acid, 2,6-dimethoxy-4-methylphenyl ester hydrochloride (1:1) salt $^1$H NMR (CDCl$_3$+C$_5$D$_5$N); δ1.67 (d, 3H), 2.33 (s, 3H), 3.15–3.35 (m, 4H), 3.37 (s, 6H), 3.55–3.65 (m, 2H), 3.7–3.85 (m, 2H), 3.78 (s, 6H), 4.25 (q, 1H), 6.41 (s, 2H), 6.5 (br, NH$^+$). [α]$_D$=+9.5° (c=0.3 in chloroform)

7z: R-(+)-2-[N-bis(2-ethoxyethyl)amino]butyric acid, 2,6-dimethoxyphenyl ester hydrochloride (1:1) salt $^1$H NMR (CDCl$_3$+C$_5$D$_5$N); δ1.12 (t, 3H), 1.20 (t, 6H), 1.95–2.10 (m, 2H), 3.1–3.3 (m, 4H), 3.52 (q, 4H), 3.5–3.7 (m, 4H), 3.75 (t, 1H), 3.79 (s, 6H), 6.3 (br, NH$^+$) 6.60 (d, 2H), 7.13 (t, 1H). [α]$_D$=+5.2° (c=0.5 in chloroform)

7aa: S-(−)-2-[N-bis(2-ethoxyethyl)amino]butyric acid, 2,6-dimethoxyphenyl ester hydrochloride (1:1) salt $^1$H NMR (CDCl$_3$+C$_5$D$_5$N); δ1.13 (t, 3H), 1.20 (t, 6H), 1.95–2.15 (m, 2H), 3.1–3.3 (m, 4H), 3.52 (q, 4H), 3.6–3.8 (m, 4H), 3.79 (s, 6H), 3.90 (t, 1H), 6.60 (d, 2H), 7.14 (t, 1H), 7.3 (br, NH$^+$). [α]$_D$=−3.0° (c=0.5 in chloroform)

7ab: R-(+)-2-[N-bis(2-methoxyethyl)amino]butyric acid, 2,6-dimethoxyphenyl ester hydrochloride (1:1) salt $^1$H NMR (CDCl$_3$+C$_5$D$_5$N); δ1.12 (t, 3H), 1.90–2.05 (m, 2H), 3.0–3.25 (m, 4H), 3.37 (s, 6H), 3.55–3.70 (m, 4H), 3.80 (s, 6H), 3.75 (t, 1H), 5.25 (br, NH$^+$), 6.60 (d, 2H), 7.15 (t, 1H). [α]$_D$=+4.6° (c=0.5 in chloroform)

7ac: R-2-[N-bis(2-methoxyethyl)amino]pentanoic acid, 2,6-dimethoxyphenyl ester hydrochloride (1:1) salt $^1$H NMR (CDCl$_3$+C$_5$D$_5$N); δ1.00 (t, 3H), 1.50–1.65 (m, 2H), 1.88–1.98 (m, 2H), 3.0–3.25 (m, 4H), 3.37 (s, 6H), 3.55–3.70 (m, 4H), 3.80 (s, 6H), 3.88 (t, 1H), 5.85 (br, NH$^+$), 6.60 (d, 2H), 7.15 (t, 1H).

7ad: (±)-2-[N-bis(2-methoxyethyl)amino]hexanoic acid, 2,6-dimethoxyphenyl ester hydrochloride (1:1) salt $^1$H NMR (CDCl$_3$); δ7.12 (t, 1H), 6.60 (d, 2H), 3.88 (t, 1H), 3.80 (s, 6H), 3.67 (m, 2H), 3.60 (m, 2H), 3.37 (s, 6H), 3.22 (m, 2H), 3.12 (m, 2H), 1.95 (m, 2H), 1.52 (m, 2H), 1.41 (m, 2H), 0.95 (t, 3H).

7ae: (±)-2-[N-bis(2-methoxypropyl)amino]butyric acid, 2,6-dimethoxyphenyl ester hydrochloride (1:1) salt $^1$H NMR (CDCl$_3$+Na$_2$CO$_3$ in D$_2$O); δ7.13 (t, 1H), 6.62 (d, 2H), 3.81 (s, 6H), 3.52 (t, 1H), 3.46 (m, 4H), 3.35 (s, 6H), 2.86 (m, 2H), 2.72 (m, 2H), 1.95 (m, 1H), 1.78 (m, 5H), 1.08 (t, 3H).

7af: (±)-2-[N-bis(2-methoxyethyl)amino]pentanoic acid, 2,6-dimethoxy-4-methylphenyl ester hydrochloride (1:1) salt $^1$H NMR (CDCl$_3$+C$_5$D$_5$N); δ1.00 (t, 3H), 1.52–1.65 (m, 2H), 1.86–2.06 (m, 2H), 2.33 (s, 3H), 3.11–3.34 (m, 4H), 3.37 (s, 6H), 3.56–3.77 (m, 4H), 3.78 (s, 6H), 3.95 (t, 1H), 6.41 (s, 2H).

7ag: (±)-2-[N-bis(2-methoxyethyl)amino]hexanoic acid, 2,6-dimethoxy-4-methylphenyl ester hydrochloride (1:1) salt $^1$H NMR (CDCl$_3$+C$_5$D$_5$N); δ0.93 (t, 3H), 1.31–1.59 (m, 4H), 1.66–1.79 (m, 1H), 1.85–1.97 (m, 1H), 2.33 (s, 3H), 2.87–3.09 (m, 4H), 3.35 (s, 6H), 3.41–3.53 (m, 4H), 3.64 (t, 1H), 3.77 (s, 6H), 6.40 (s, 2H).

7ah: ξ-2-[N-bis(2-methoxyethyl)amino]hexanoic acid, 2,6-dimethoxyphenyl ester hydrochloride (1:1) salt. (the symbol ξ is used to indicate the compound to be enantiomerically pure, but with unknown stereochemistry; 7ai represents the second enantiomer). $^1$H NMR (CDCl$_3$); δ0.94 (t, 3H), 1.35–1.60 (m, 4H), 1.86–2.02 (m, 2H), 3.02–3.24 (m, 4H), 3.37 (s, 6H), 3.51–3.66 (m, 4H), 3.80 (s, 6H), 3.83 (t, 1H), 6.60 (d, 2H), 7.11 (t, 1H).

7ai: ξ-2-[N-bis(2-methoxyethyl)amino]hexanoic acid, 2,6-dimethoxyphenyl ester hydrochloride (1:1) salt
$^1$H NMR (CDCl$_3$+Na$_2$CO$_3$ in D$_2$O); δ0.94 (t, 3H), 1.33–1.57 (m, 4H), 1.64–1.78 (m, 1H), 1.86–1.96 (m, 1H), 2.86–3.09 (m, 4H), 3.36 (s, 6H), 3.40–3.53 (m, 4H), 3.64 (t, 1H), 3.80 (s, 6H), 6.60 (d, 2H), 7.12 (t, 1H).

7aj: (±)-2-[N-bis(2-methoxyethyl)amino]4-methylpentanoic acid, 2,6-dimethoxy-4-methylphenylester hydrochloride (1:1) salt
$^1$H NMR (CDCl$_3$); δ0.98–1.03 (m, 6H), 1.82–1.88 (m, 2H), 1.90–1.98 (m, 1H), 2.33 (s, 3H), 3.08–2.16 (m, 2H), 3.20–3.27 (m, 2H), 3.37 (s, 6H), 3.55–3.60 (m, 2H), 3.66–3.72 (m, 2H), 3.77 (s, 6H), 3.98–4.03 (m, 1H), 6.40 (s, 2H).

7ak: (±)-2-[N-(2-methoxyethyl)-N-methylamino]-4-methylpentanoic acid, 2,6-dimethoxy-4-methylphenylester hydrochloride (1:1) salt
$^1$H NMR (CDCl$_3$); δ1.01 (d, 3H), 1.06 (d, 3H), 1.88–2.08 (m, 3H), 2.35 (s, 3H), 2.87 (s, 3H), 3.22–3.35 (m, 2H), 3.39 (s, 3H), 3.78 (s, 6H), 3.82–3.87 (m, 2H), 4.03–4.10 (m, 1H), 6.43 (s, 2H).

7al: (±)-2-[N-bis(2-methoxyethyl amino]-3-methylbutyric acid, 2,6-dimethoxy-4-methylphenylester hydrochloride (1:1) salt
$^1$H NMR (CDCl$_3$); δ1.04–1.06 (m, 6H), 2.02–2.11 (m, 1H), 2.33 (s, 3H), 2.82–2.89 (m, 2H), 2.96–3.03 (m, 2H), 3.12 (d, 1H), 3.35 (s, 6H), 3.41–3.51 (m, 4H), 3.77 (s, 6H), 6.41 (s, 2H).

7am: (±)-2-[N-bis(2-methoxyethyl)amino]-4-methylpentanoic acid, 2,6-dimethoxyphenylester hydrochloride (1:1) salt
$^1$H NMR (CDCl$_3$+Na$_2$CO$_3$ in D$_2$O); δ0.96–1.00 (m, 6H), 1.61–1.68 (m, 1H), 1.73–1.81 (m, 1H), 1.85–1.96 (m, 1H), 2.90–2.97 (m, 2H), 3.00–3.07 (m, 2H), 3.36 (s, 6H), 3.42–3.53 (m, 4H), 3.77 (t,1H), 3.79 (s, 6H), 6.60 (d, 2H), 7.11 (t,1H).

7an: (±)-2-[N-(2-methoxyethyl)-N-methylamino]-4-methylpentanoic acid, 2,6-di-methoxyphenylester hydrochloride (1:1) salt
$^1$H NMR (CDCl$_3$+Na$_2$CO$_3$ in D$_2$O); δ0.97–1.01 (m, 6H), 1.58–1.66 (m, 1H), 1.79–1.92 (m, 2H), 2.52 (s, 3H), 2.78–2.85 (m,1H), 2.98–3.04 (m, 1H), 3.38 (s, 3H), 3.45–3.58 (m, 2H), 3.66 (t, 1H), 3.80 (s, 6H), 6.60 (d, 2H), 7.12 (t, 1H).

Example 8

Hypnotic Activity

The hypnotic potency of the α-amino acid phenyl ester derivatives of the invention was determined upon their intravenous administration in mice. The dose required to cause a loss of righting reflex for a minimum period of 30 seconds in 50% of treated mice after intravenous injection over 10 seconds was determined. This dose is termed the HD$_{50}$ (hypnotic dose$_{50}$) and is expressed in μmol.kg$^{-1}$. These in vivo experiments were carried out as described in detail by Anderson et al., J.Med.Chem. 1997, 40, 1668–1681. The in vivo HD$_{50}$ data for a number of compounds of the invention are given in Table I.

The in vitro effect of the compounds of the invention at GABA$_A$ receptors was assessed through determination of their ability to inhibit [$^{35}$S]-TBPS ([$^{35}$S]-tert-butyl bicyclophosphorothionate) binding to rat whole brain membranes. The concentration of α-amino acid phenyl ester derivative required to inhibit 50% of binding of [$^{35}$S]-TBPS was determined. These in vitro experiments were carried out as described in detail by Anderson et al., J.Med.Chem. 1997, 40, 1668–1681. IC$_{50}$ data for a number of compounds of the invention are given in Table I.

TABLE I

Formula I

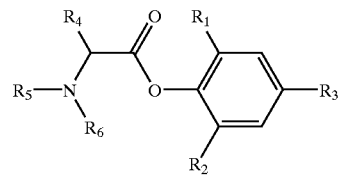

| Example[1] | R$_3$ | R$_4$ | R$_5$ | R$_6$ | TBPS IC$_{50}$ μM | HD50 μmol.kg$^{-1}$ |
|---|---|---|---|---|---|---|
| 7a | Me[5] | Et | CH$_2$—CH$_2$—O—Me | CH$_2$—CH$_2$—O—Me | 22 | 21 |
| 7v | # | # | # | # | 14 | 35 |
| 7b | # | # | # | # | 18 | 22 |
| 7c | H | Et | CH$_2$—CH$_2$—O—Me | CH$_2$—CH$_2$—O—Me | 10 | 19 |
| 7l | H | Et | CH$_2$—CH$_2$—O—Et | CH$_2$—CH$_2$—O—Et | ND[4] | 29 |
| 7z | # | # | # | # | 18 | 19 |
| 7aa | # | # | # | # | 11 | 22 |
| 7s | H | n-Pr | CH$_2$—CH$_2$—O—Me | CH$_2$—CH$_2$—O—Me | 4.2 | 12 |
| 7d | H | Me | CH$_2$—CH$_2$—O—Et | CH$_2$—CH$_2$—O—Et | ≦100 | 68 |
| 7x | # | # | # | # | <100 | 46 |
| 7w | # | # | # | # | ~100 | 35 |
| 7e | Me | Me | CH$_2$—CH$_2$—O—Me | CH$_2$—CH$_2$—O—Me | <100 | 52 |
| 7f | H | Me | CH$_2$—CH$_2$—O—Me | CH$_2$—CH$_2$—O—Me | <100 | 55 |
| 7y | Me | Me | CH$_2$—CH$_2$—O—Me | CH$_2$—CH$_2$—O—Me | <100 | 18 |
| 7g | Me | Me | Me | benzyl | 22 | 45 |

TABLE I-continued

Formula I

![Formula I structure showing R4, R5-N-R6, with ester linkage to phenyl ring bearing R1, R2, R3]

| Example[1] | R$_3$ | R$_4$ | R$_5$ | R$_6$ | TBPS IC$_{50}$ µM | HD50 µmol.kg$^{-1}$ |
|---|---|---|---|---|---|---|
| 7h | # | # | # | # | 27 | 56 |
| 7k | H | Et | Me | benzyl | 13 | 40 |
| 7m | H | Me | Me | CH$_2$—CH$_2$-phenyl | 59 | 38 |
| 7p | Me | Me | Me | CH$_2$—CH$_2$—O—Me | ~100 | 72 |
| 7l | Me | Me | Me | CH$_2$—CH=CH$_2$ | ~100 | 60 |
| 7j | Me | Me | Et | Et | <50 | 43 |
| 7t | OMe | Et | CH$_2$—CH$_2$—O—Me | CH$_2$—CH$_2$—O—Me | 14 | 21 |
| 7n[2] | H | Et | CH$_2$—CH$_2$—O—Me | CH$_2$—CH$_2$—O—Me | 20 | 27 |
| 7u | H | i-Pr | CH$_2$—CH$_2$—O—Me | CH$_2$—CH$_2$—O—Me | 100 | 27 |
| 7o[3] | H | Et | CH$_2$—CH$_2$—O—Me | CH$_2$—CH$_2$—O—Me | <100 | 64 |
| 7ad | H | n-Bu | CH$_2$—CH$_2$—O—Me | CH$_2$—CH$_2$—O—Me | ND | <12 |
| 7ae | H | Et | (CH$_2$)$_3$OMe | (CH$_2$)$_3$OMe | ND | 27 |
| 7af | Me | n-Pr | CH$_2$—CH$_2$—O—Me | CH$_2$—CH$_2$—O—Me | ND | 34 |
| 7ag | Me | n-Bu | CH$_2$—CH$_2$—O—Me | CH$_2$—CH$_2$—O—Me | ND | 34 |
| 7ah | H | n-Bu | CH$_2$—CH$_2$—O—Me | CH$_2$—CH$_2$—O—Me | ND | 8 |
| 7ai | H | n-Bu | CH$_2$—CH$_2$—O—Me | CH$_2$—CH$_2$—O—Me | ND | 47 |
| 7aj | Me | i-Bu | CH$_2$—CH$_2$—O—Me | CH$_2$—CH$_2$—O—Me | ND | convulsant |
| 7ak | Me | i-Bu | Me | CH$_2$—CH$_2$—O—Me | ND | 28 |
| 7al | Me | i-Pr | CH$_2$—CH$_2$—O—Me | CH$_2$—CH$_2$—O—Me | ND | 44 |
| Reference* | | | | | 766 | 139 |

[1]R$_1$ and R$_2$ are each OMe if not otherwise indicated;
[2]R$_1$ and R$_2$ are each OEt;
[3]R$_1$ and R$_2$ are each O-i-Pr
[4]N.D — not determined
*Reference: 2,6-dimethoxyphenyl 2-morpholinopropionate (GB Patent 1,160,468)
[5]Me = methyl; Et = ethyl; n-Pr = n-propyl; i-Pr = iso-propyl; n-Bu = n-butyl; i-Bu = iso-butyl

What is claimed is:

1. An α-amino acid pheny ester compound selected from

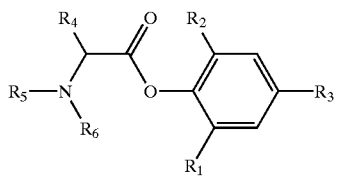

wherein
R$_1$ is (C$_{1-3}$)alkoxy;
R$_2$ is (C$_{1-3}$)alkyl, (C$_{1-3}$)alkoxy or (C$_{2-3}$)alkenyl;
R$_3$ is hydrogen, (C$_{1-3}$)alkyl, (C$_{1-3}$)alkoxy or (C$_{2-3}$) alkenyl;
R$_4$ is (C$_{1-6}$)alkyl;
R$_5$ and R$_6$ are independently butyl, isobutyl, tertiary butyl, pentyl, hexyl, (C$_{1-6}$)alkyl substituted with (C$_{1-3}$)alkoxy, (C$_{1-3}$)alkoxycarbonyl, cyano or NR$_7$, R$_8$(C$_{2-6}$)alkenyl, (C$_{2-6}$)alkenyl substituted with (C$_{1-3}$) alkoxy, (C$_{1-3}$)alkoxycarbonyl, cyano or NR$_7$R$_8$, (C$_{2-6}$) alkynyl (C$_{2-6}$)alkynyl substituted with (C$_{1-3}$)alkoxy, (C$_{1-3}$)alkoxycarbonyl, cyano or NR$_7$R$_8$, aralkyl or aralkyl substituted with (C$_{1-3}$)alkoxy, (C$_{1-3}$) alkoxycarbonyl, cyano or NR$_7$R$_8$;
R$_7$ and R$_8$ are independently (C$_{1-6}$)alkyl; and
a pharmaceutically acceptable salt thereof.

2. The α-amino acid phenyl compound of claim 1, wherein R$_1$ and R$_2$ are methoxy and R$_4$ is (C$_{2-3}$)alkyl.

3. The α-amino acid phenyl compound of claim 1, wherein R$_3$ is hydrogen or methyl and R$_5$ and R$_6$ are methoxyethyl or ethoxyethyl.

4. The α-amino acid phenyl compound of claim 2, wherein R$_3$ is hydrogen or methyl and R$_5$ and R$_6$ are methoxyethyl or ethoxyethyl.

5. The α-amino acid phenyl compound of claim 1, wherein R$_1$ and R$_2$ are methoxy, R$_3$ is hydrogen or methyl, R$_4$ is ethyl and R$_5$ and R$_6$ are methoxyethyl.

6. The α-amino acid phenyl compound of claim 5, wherein the configuration at the α-carbon atom is that of the R-enantiomer.

7. A pharmaceutical composition comprising the α-amino acid phenyl compound of claim 1 or a pharmaceutically acceptable salt thereof and at least one pharmaceutically acceptable auxiliary.

8. A method for inducing an anaesthetic, sedative, analgesic or seizure alleviating effect in a mammal, comprising administering an effective amount of the α-amino acid phenyl ester compound of claim 1, or a pharmaceutically acceptable salt thereof.

9. A method for treating GABA related diseases selected from the group consisting of anxiety, stress, sleep disorders, post-natal depression, seizure, and premenstrual tension, comprising administering an effective amount of the α-amino acid phenyl ester compound of claim 1, or a pharmaceutically acceptable salt thereof.

* * * * *